(12) United States Patent
Kim et al.

(10) Patent No.: US 10,351,855 B2
(45) Date of Patent: Jul. 16, 2019

(54) PHARMACEUTICAL COMPOSITION FOR INHIBITION OF CANCER CELL METASTASIS INCLUDING SIRNA FOR RIBOSOMAL PROTEIN S3

(71) Applicant: Joon Kim, Seoul (KR)

(72) Inventors: Joon Kim, Seoul (KR); Hag Dong Kim, Gyeonggi-do (KR); YongJoong Kim, Seoul (KR)

(73) Assignee: Joon Kim, Seoul (KR)

( * ) Notice: Subject to any disclaimer, the term of this patent is extended or adjusted under 35 U.S.C. 154(b) by 0 days.

(21) Appl. No.: 15/629,369

(22) Filed: Jun. 21, 2017

(65) Prior Publication Data

US 2018/0346915 A1   Dec. 6, 2018

(30) Foreign Application Priority Data

Jun. 2, 2017   (KR) .................. 10-2017-0069292

(51) Int. Cl.
*C07H 21/04* (2006.01)
*C12N 15/113* (2010.01)

(52) U.S. Cl.
CPC .. *C12N 15/1137* (2013.01); *C12Y 402/99018* (2013.01); *C12N 2310/14* (2013.01)

(58) Field of Classification Search
CPC .................................................... A61K 48/00
See application file for complete search history.

(56) References Cited

U.S. PATENT DOCUMENTS 7,691,997 B2 *   4/2010   Khvorova ............ A61K 31/713
536/24.5

OTHER PUBLICATIONS

Kim et al., Ribosomal protein S3 (rpS3) secreted from various cancer cells is N-linked glycosylated, Research Paper, Jun. 22, 2016, p. 80350-80362, vol. 7(No. 49), Oncotarget.

Fire A.et al., Potent and specificgenetic interference by double-stranded RNA in Caenorhabditis elegans, Feb. 19, 1998, p. 806-811, vol. 391, Nature.
Kim et al.,Implication of mammalian ribosomal protein S3 in the processing of DNA damage, Journal,Jun. 9, 1995,p. 13620-9, vol. 270 No. 23.,The Journal of Biological Chemstry.
Xiaofei et al.,Bacterial Effector Binding to Ribosomal Protein S3 Subverts NF-kB Function, Dec. 2009, p. 1-18, vol. 5 Issue 12, PLoS Pathogens.
Kim et al., PKCσ-dependent functional switch of rpS3 between translation and DNA repair, Nov. 19, 2008, p. 395-405, Biochimica et Biophysica Acta 1793.
Yang et al., Phosphorylation of Ribosomal Protein S3 and Antiapoptotic TRAF2 Protein Mediates Radioresistance in Non-small Cell Lung Cancer Cells. Journal, Feb. 1, 2013, p. 2965-2975, vol. 288, No. 5, The Journal of Biological Chemstry.
Lee et al., Ribosomal Protein S3, a New Substrate of Akt, Serves as a Signal Mediator between Neuronal Apoptosis and DNA Repair, Journal, Sep. 17, 2010, p. 29457-29468 vol. 285, No. 38, The Journal of Biological Chemstry.
Jang et al., Ribosomal protein S3 localizes on the mitotic spindle and functions as a microtubule associated protein in mitosis, Nov. 3, 2012, p. 57-62, Biochemical and Biophysical Research Communications 429.
Higgins et al., The Unfolded Protein Response Triggers Site-Specific Regulatory Ubiquitylation of 40S Ribosomal Proteins, Jul. 2, 2015, p. 35-49, Molecular Cell 59.
Sui et al., A DNA vector-based RNAi technology to suppress gene expression in mammalian cells, Apr. 16, 2002, p. 5515-5520, vol. 99 No. 8, PNAS.
Brummelkamp et al., A System for Stable Expression of Short Interfering RNAs in Mammalian Cells, Apr. 19, 2002, p. 550-553, vol. 296, Science.
Paul et al., Effective expression of small interfering RNA in human cells, May 2002, p. 505-508, vol. 20, Nature Biotechnology.

* cited by examiner

*Primary Examiner* — Kimberly Chong
(74) *Attorney, Agent, or Firm* — IP & T Group LLP

(57) ABSTRACT

The present invention relates to a pharmaceutical composition for inhibiting cancer cell metastasis, the pharmaceutical composition including at least one of: (1) si-rpS3/203 binding to a $203^{rd}$ base sequence of rpS3 mRNA; (2) si-rpS3/635 binding to a base sequence corresponding to a position 635 of the rpS3 mRNA; (3) si-rpS3/747 binding to a base sequence corresponding to a position 747 of the rpS3 mRNA; and (4) si-rpS3/766 binding to a base sequence corresponding to a position 766 of the rpS3 mRNA.

2 Claims, 4 Drawing Sheets

Specification includes a Sequence Listing.

SEQUENCE LISTING

```
<160> NUMBER OF SEQ ID NOS: 8

<210> SEQ ID NO 1
<211> LENGTH: 21
<212> TYPE: DNA
<213> ORGANISM: HUMAN

<400> SEQUENCE: 1
aactgactgc tgtagttcag a                                            21
```

```
<210> SEQ ID NO 2
<211> LENGTH: 21
<212> TYPE: DNA
<213> ORGANISM: HUMAN

<400> SEQUENCE: 2
aacccaaaga tgagatactg c                                              21

<210> SEQ ID NO 3
<211> LENGTH: 19
<212> TYPE: DNA
<213> ORGANISM: HUMAN

<400> SEQUENCE: 3
cagctgtatt ctggagtct                                                 19

<210> SEQ ID NO 4
<211> LENGTH: 19
<212> TYPE: DNA
<213> ORGANISM: HUMAN

<400> SEQUENCE: 4
ggatgttgct ctctaaaga                                                 19

<210> SEQ ID NO 5
<211> LENGTH: 23
<212> TYPE: PRT
<213> ORGANISM: HUMAN

<400> SEQUENCE: 5

Ala Ala Ala Gly Gly Ala Thr Cys Cys Thr Thr Ala Thr Gly Cys Thr
1               5                   10                  15

Gly Thr Gly Gly Gly Gly Ala
            20

<210> SEQ ID NO 6
<211> LENGTH: 24
<212> TYPE: PRT
<213> ORGANISM: HUMAN

<400> SEQUENCE: 6

Ala Gly Cys Ala Gly Thr Gly Thr Cys Ala Ala Cys Gly Thr Ala Gly
1               5                   10                  15

Thr Ala Gly Cys Cys Ala Ala Cys
            20

<210> SEQ ID NO 7
<211> LENGTH: 21
<212> TYPE: PRT
<213> ORGANISM: HUMAN

<400> SEQUENCE: 7

Ala Gly Cys Gly Gly Ala Gly Ala Cys Cys Cys Thr Gly Thr Thr Gly
1               5                   10                  15

Gly Cys Thr Ala Cys
            20

<210> SEQ ID NO 8
<211> LENGTH: 30
<212> TYPE: PRT
<213> ORGANISM: HUMAN
```

-continued

```
<400> SEQUENCE: 8

Thr Thr Thr Gly Gly Ala Thr Cys Cys Thr Thr Ala Gly Ala Thr Ala
1               5                   10                  15

Ala Thr Gly Ala Thr Thr Thr Cys Thr Gly Thr Cys Cys Thr
            20                  25                  30
```

PHARMACEUTICAL COMPOSITION FOR INHIBITION OF CANCER CELL METASTASIS INCLUDING SIRNA FOR RIBOSOMAL PROTEIN S3

CROSS-REFERENCE TO RELATED APPLICATION(S)

The present application claims priority to Korean Patent Application No. 10-2017-0069292, filed on Jun. 2, 2017, which is herein incorporated by reference in its entirety.

BACKGROUND OF THE INVENTION

1. Field of the Invention

The present invention relates to a pharmaceutical composition for inhibiting cancer cell metastasis, and more particularly, to a pharmaceutical composition for inhibiting cancer metastasis by controlling proteins related to cancer metastasis using a small interference RNA (siRNA) for specifically inhibiting the expression of proteins present in a cell.

2. Description of the Related Art

A small interference RNA (siRNA) is a substance for inducing an RNA interference (RNAi), and refers to a short double-strand RNA consisting of about a dozen of base sequences to about several tens of base sequences.

The RNAi is a scheme of regulating a post-transcriptional gene which is conserved in a plurality of eukaryotic organisms, and refers to a phenomenon in which a predetermined double-strand RNA is introduced into cells so as to induce the selective degradation of an mRNA of a target gene or selectively inhibit the expression of the target gene. The predetermined double-strand RNA includes a sense RNA having a sequence homologous to a messenger RNA (mRNA) of a target gene and an anti-sense RNA having a sequence complementary to the sense RNA (Fire A. et al., Nature, 391: 806-811, 1998).

Because the RNAi can selectively inhibit the expression of the target gene, the RNAi takes an important role as a simple gene knock-down scheme substituting for a conventional gene destruction scheme based on an inefficient homologous recombination, and inhibits the gene expression of the mRNA of the target gene having the base sequence complementary to the base sequence of the siRNA by injecting the siRNA into a cell. In addition, it is important that the RNAi can be applied to a therapeutic agent for a specific protein-involved disease.

A ribosomal protein small subunit 3 (rpS3) is a protein constituting ribosome, and it is also known as an enzyme which recovers damaged DNA (Kim et al., 1995 J. Biol. Chem. 270(23) 13620-9). The rpS3 is known to take various roles in cancer cell metastasis, apoptosis, and transcription in an immune response.

Recently, it is known that the various roles of the rpS3 can be regulated through modifications such as phosphorylation, methylation, monoubiquitination, and glycosylation (Xiaofei et al., 2009 PLoS Pathog. 5(12) e100070; Kim et al., 2009 BBA-Mol. Cell Res. 1793(2), 395405; Yang et al., 2013 J. Biol. Chem. 288, 2965-2975; Lee et al., 2010 J. Biol. Chem. 285(38), 29457-68; Shin et al., 2009 Biochem Biophys Res Commun. 429(1-2), 57-62; and Higgins et al., 2015 Mol. Cell. 59(1), 35-49, etc.).

SUMMARY OF THE INVENTION

The present invention provides a pharmaceutical composition for inhibiting a cancer cell metastasis.

The pharmaceutical composition of the present invention is a pharmaceutical composition for inhibiting a cancer cell metastasis including at least one of the following (1) to (2):

(1) si-rpS3/203 binding to a base sequence corresponding to the position 203 of rpS3 mRNA, wherein the si-rpS3/203 is represented by a base sequence of SEQ ID NO: 1, and (2) si-rpS3/635 binding to a base sequence corresponding to the position 635 of the rpS3 mRNA, wherein the si-rpS3/635 is represented by a base sequence of SEQ ID NO: 2.

The pharmaceutical composition for inhibiting the cancer cell metastasis may include the si-rpS3/203, wherein the Si-rpS3/203 is represented by a base sequence of SEQ ID NO: 1.

The si-rpS3/203 may inhibit the expression of the rpS3 at the level of the messenger RNA (mRNA) of the rpS3.

The pharmaceutical composition for inhibiting the cancer cell metastasis may include the si-rpS3/635, wherein the Si-rpS3/635 is represented by a base sequence of SEQ ID NO: 2.

The si-rpS3/635 may inhibit the expression of the rpS3 at the level of the messenger RNA (mRNA) of the rpS3.

The inventors of the present invention recently have studied and found that the rpS3 is rarely secreted in a normal cell, however, large amounts of rpS3 are secreted in malignant tumor cells where metastasis frequently occurs.

The rpS3 is N-link glycosylated at a residue of asparagine amino acid which is the $165^{th}$ amino acid constituting the rpS3, and secreted out of the cells via an ER-Golgi secretion pathway. The cancer cell metastasis occurs by the secreted rpS3, and an inhibition of the rpS3 expression by siRNA reduces secretions of cancer cells.

The secretion of the rpS3 is very important for the metastasis and malignancy in the cancer cells. A protein modification via the glycosylation of the asparagine which is the $165^{th}$ amino acid of the rpS3 takes an important role on regulating the secretion of the rpS3.

In order to prepare the si-RNA capable of regulating the rpS3 protein, which takes an important role on the metastasis and malignancy in the cancer cells, at the mRNA level, the inventors of the present invention prepared si-RNA starting from $203^{rd}$ and $635^{th}$ nucleotides by using a sequence analysis, based on the transcription start codon AUG of a human rpS3 gene (Genbank accession number NM_001005.4). In addition, the inventors of the present invention prepared si-RNA starting from $747^{th}$ and $766^{th}$ nucleotides by using the sequence analysis, based on the transcription start codon AUG of the human rpS3 gene (Genbank accession number NM_001005.4).

Because the prepared si-RNA may specifically recognize the sequences of an open reading frame and a 3' untranslated region of the rpS3 mRNA, the expressed rpS3 protein can be specifically recognized and reduced by using the si-RNA.

The prepared si-RNA may not only has a completely complementary binding to the target mRNA, but also include a portion which does not form a pair caused by a mismatch (the corresponding bases are not complementary) or a bulge (a base corresponding to a strand of one side is not present).

The prepared si-RNA may be a double-strand RNA in which the nucleotide length is 10 to 40 nucleotide lengths capable of inhibiting the activity and expression of the rpS3, preferably, 15 to 30 nucleotide lengths, more preferably, 19 to 21 nucleotide lengths. The length of the si-RNA refers to a length of the nucleotide forming a double strand (pairing).

A terminal structure of the prepared si-RNA may be blunt or cohesive as long as the terminal structure can inhibit the expression of the target gene by an RNAi effect. The cohesive terminal structure may have a configuration where a 3' terminal side is overhung or a 5' terminal side is overhung. The number of overhung nucleotides is not limited, however, may be, for example, 1 to 8 nucleotides, preferably, 1 to 4 nucleotides.

In addition, within a range for maintaining the effect of inhibiting the expression of the target gene, the siRNA may include, for example, dTdT or UU at an overhang portion of one end of the siRNA, or include a sequence that continuously matches with or complementary to the rpS3 mRNA at a double-strand portion.

The siRNA does not need to have cleavage terminal structures at both sides thereof, and may have stem-loop type structures where one terminal portion of the double-strand RNA is connected by a linker RNA. There is no special limitation in the length of the linker as long as the length does not hinder the pairing of the stem portions.

The siRNA of the present invention may be chemically modified by conventional methods known in the art so as to prevent rapid degradation caused by in-vivo nucleases and improve in-vivo stability.

For example, the hydroxyl group at a 2'-position of sugar (ribose ring) of at least one nucleotide included in the siRNA may be substituted with hydrogen atom, halogen atom, —O-alkyl group, —O-acyl group or an amino group, and more specifically, with H, OR, R, R'OR, SH, SR, $NH_2$, NHR, $NR_2$, $N_3$, CN, F, Cl, Br, I and so on (herein, R may be alkyl or aryl, preferably, an alkyl group having 1 to 6 carbon atoms, and R' may be alkylene, preferably, may be alkylene having 1 to 6 carbon atoms), or a phosphate backbone may be substituted with phosphorothioate, phosphorodithioate, alkyl phosphonate, phosphoamidate, boranophosphate or the like.

As an example of the chemical modification of the siRNA, the phosphodiester binding of the siRNA sense or anti-sense strand may be substituted with the boranophosphate or phosphorothioate, thus a resistance against nucleic acid degradation is increased. For example, the modification may be applied to a 3' terminal, 5' terminal or both terminals of the siRNA sense or anti-sense strand, preferably, to a terminal position of RNA such as a 3' terminal overhang (for example, $(dT)n$, n is an integer ranging from 1 to 5, preferably from 2 to 4).

For another example, an ethylene bridge nucleic acid (ENA) or a locked nucleic acid (LNA) may be applied to the 5' terminal, 3' terminal or both terminals of the siRNA sense or anti-sense strand, preferably, the 5' terminal of the siRNA sense strand. Thus, the siRNA stability can be increased and the immune response and the non-specific inhibitory effect can be reduced without exerting an influence on the RNAi ability.

The prepared siRNA may include at least one variant having substitution, insertion, deletion or combinations thereof, in which the variant is a functional equivalent having a variation for preventing the siRNA activity from being deteriorated. For example, the prepared siRNA may represent a homology of at least 80%, preferably at least 90%, and more preferably at least 95%, with respect to the siRNA of the corresponding sequence number. The homology may be easily determined by comparing the nucleotide sequence with the corresponding part of the target gene by using a computer algorithm widely known in the art of the present invention, for example, the Align or BLAST algorithm.

In order to prepare the siRNA, various methods generally known in the art can be adopted, such as a direct chemical synthesis method (Sui G et al., Proc Natl Acad Sci USA, 99: 5515-5520, 2002), a synthesis method using an in vitro transcription (Brummelkamp T R et al., Science, 296: 550-553, 2002), a method in which a long double-strand RNA synthesized by the in vitro transcription is cleaved by using RNaseIII family enzyme (Paul C P et al., Nature Biotechnology, 20: 505-508, 2002), and so on.

According to the present invention, rpS3 secreted from a cancer cell can be inhibited at an mRNA level.

According to the present invention, the metastasis and malignancy of the cancer cell can be inhibited.

DETAILED DESCRIPTION OF THE INVENTION

Figure 1:
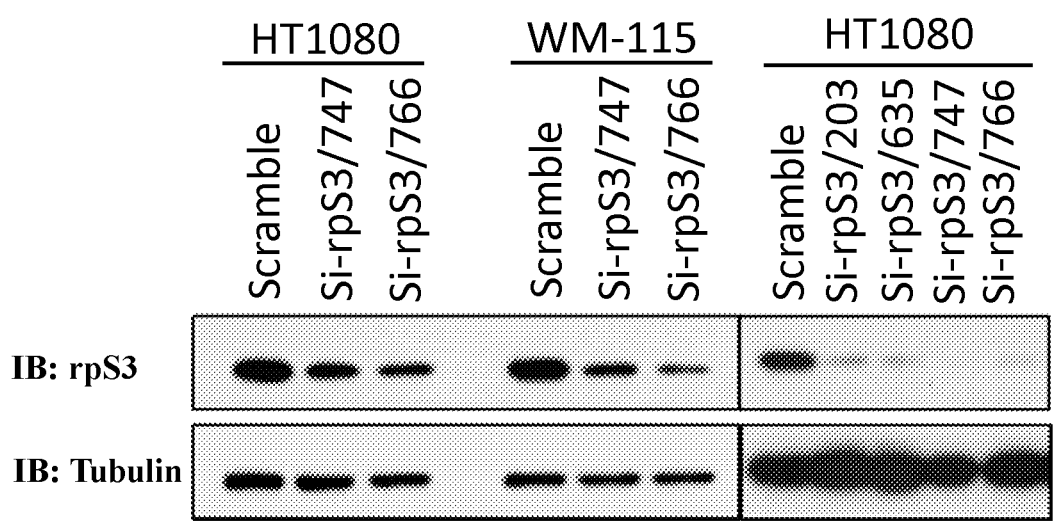
FIG. 1 is an image showing the result in which the protein expression is specifically inhibited in the rpS3 by prepared si-rpS3s in a human fibrosarcoma cell line and a human skin melanoma cell line.

Hereinafter, the present invention will be described in more detail with reference to examples and drawings. It will be obvious that the purpose of the following examples is just to specifically describe the present invention in detail and the examples are not to be construed to limit the scope of the present invention.

Example 1: Protein Modification Through Glycosylation of $165^{th}$ Glycine Amino Acid Related to Secretion of rpS3

An LC-MS/MS scheme was performed by concentrating only the rpS3 protein secreted by an immunoprecipitation scheme through an antibody against the rpS3 protein from a culture medium of a cancer cell line cultured by the research team of the present invention.

It was confirmed that the rpS3 protein secreted through the performed scheme is subject to the protein modification through a glycosylation process occurred at the $165^{th}$ asparagine amino acid.

Example 2: Preparation of Si-rpS3/203, 635, 747, and 766 (SEQ ID Nos: 1-4, Respectively) which are Si-RNAs for Reducing the Expression of rpS3 Protein Expressed in Cancer Cell Line In order to regulate the expression of the rpS3 protein in the cancer cell line at the mRNA level, si-RNAs (Si-rpS3/203 and si-rpS3/635) each constituting 21 nucleotides starting from the $203^{th}$ and $635^{th}$ nucleotides of the rpS3 mRNA were prepared, respectively, through a sequence analysis.

Particularly, the prepared si-RNAs are open reading frames (ORFs) which are portions included in the translation into proteins of the rpS3 mRNA, and Si-rpS3/747 and si-rpS3/766 starting from the $747^{th}$ and $766^{th}$ nucleotides are portions included in an untranslated region (UTR).

Each sequence is shown in Table 1.

| Sequence Identifier | | si-RNA sequence | Started matching site |
|---|---|---|---|
| si-rpS3/203 | SEQ ID NO: 1 | aac tga ctg ctg tag ttc aga | 203$^{rd}$ nucleotide of the ORF |
| si-rpS3/635 | SEQ ID NO: 2 | aac cca aag atg aga tac tgc | 635$^{th}$ nucleotide of the ORF |
| si-rpS3/747 | SEQ ID NO: 3 | cag ctg tat tct gga gtc t | 747$^{th}$ nucleotide of the UTR |
| si-rpS3/766 | SEQ ID NO: 4 | gga tgt tgc tct cta aag a | 766$^{th}$ nucleotide of the UTR |

Experimental Example 1: Implementation of Regulating the Protein Expression by Using Si-rpS3/203, 635, 747, and 766 which are Si-RNAs of the rpS3 Protein In order to confirm whether the si-rpS3/203, 635, 747 and 766, SEQ ID NO. 1, 2, 3, and 4, respectively, which are the si-RNAs obtained in Example 2 can regulate the expression of the rpS3 protein, 50 pmol of the si-RNA was injected into the human fibrosarcoma cell line (HT1080) and the human skin melanoma cell line (WM115) and then cultured for 48 hours.

Then, the cells were inserted into Tris-NaCl-NP40 buffer (TNN buffer) containing protease inhibitors, and dissolved through a freeze-thawing scheme.

The cell lysate obtained through the above process was quantified to prepare total cell protein of 20 g, an electrophoresis was performed in 12% SDS acrylamide gel, and the cell lysate was moved to a nitrocellulose membrane.

The total cell protein rooted on the nitrocellulose membrane was subject to a blocking reaction for one hour using a blocking solution formed of dried skim milk, and reacted with a solution, in which a polyclonal rpS3 antibody was diluted at a concentration of 0.2 g/mL, for one hour at the room temperature.

Those samples were treated with horseradish peroxidase conjugated goat anti-rabbit and anti-mouse IgG serum for one hour at the room temperature, treated with chemiluminescence substrate (Roche Diagnostics cat. #1 501 399), and sensitized to an X-ray film (FIG. 1).

According to the experimental result, the si-rpS3/203, 635, 747 and 766, which are the si-RNAs for the rpS3 protein prepared in the present invention, can specifically inhibit the protein expression in the rpS3 in the human fibrosarcoma cell line (HT1080) and the human skin melanoma cell line (WM115).

Experimental Example 2: Examination of Changing Aspects of Malignancy Patterns of the Cancer Cell Lines by Using Si-rpS3/203, 635, 747, and 766 of the Present Invention As confirmed in Experimental Example 1, in order to examine the changing aspects of malignancy patterns of the cancer cell lines by using the Si-rpS3/203, 635, 747, and 766, (SEQ ID NO. 1, 2, 3, and 4 respectively) which are the si-RNAs for the rpS3 protein prepared in Example 2, the protein expression is inhibited by modulating mRNA levels, and then cell shapes of the human fibroblastoma cell line (HT1080) and the human skin melanoma cell line (WM115) were confirmed using a 3D culturing scheme.

The cells were pretreated with 300 L of matrigel in a culture container having 24 culture grooves, cultured and solidified for 15 minutes at the temperature of 37° C. Then, 600 L of a culture medium containing 2% matrigel together with $0.1 \times 10^4$ cells is added and cultured for seven days. Then, shape changes of the cells in the culture vessel were observed through a microscope.

A surface of a cancer cell which can be metastasized protrudes, however, a surface of a normal cell which cannot be metastasized has a rounded shape.

Figure 2A:
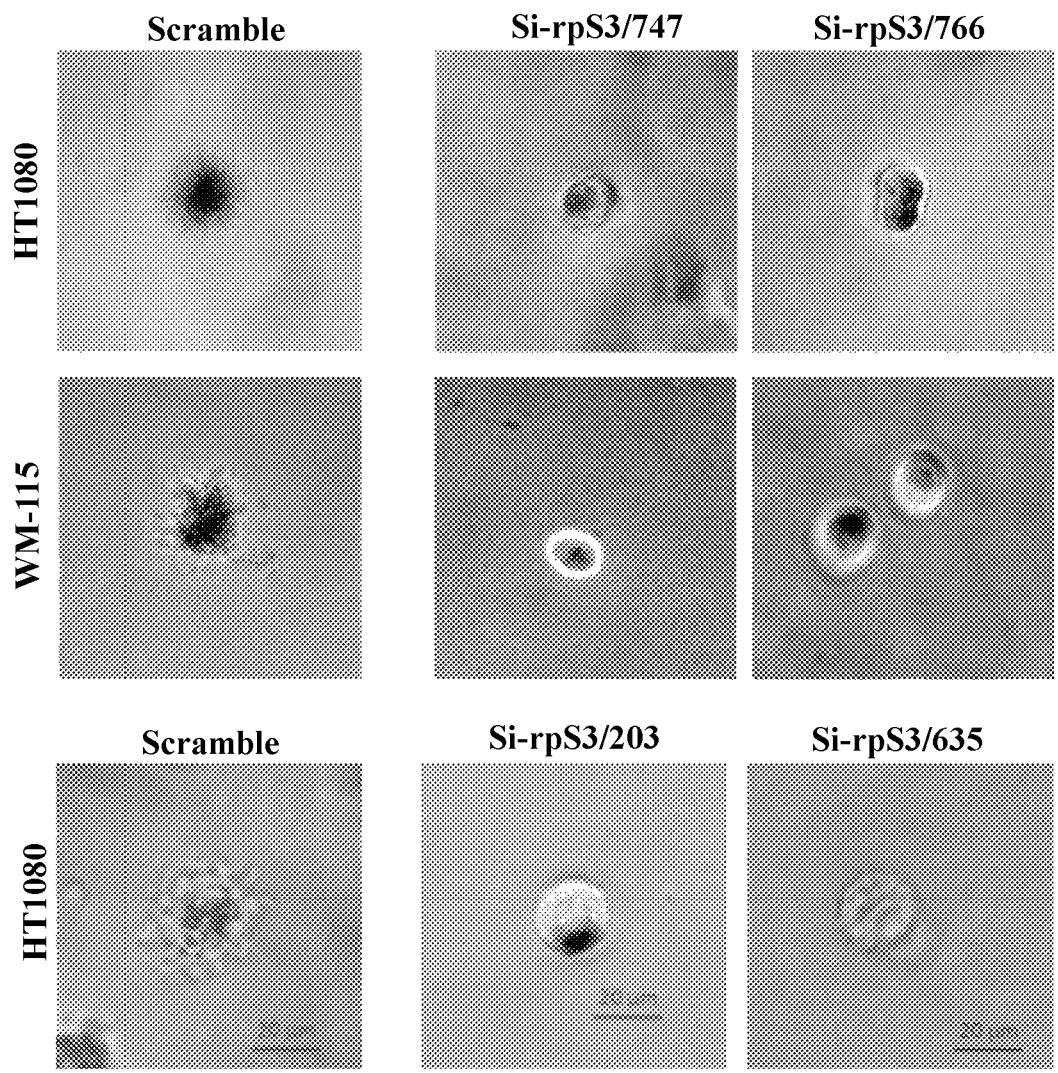
FIGS. 2A to 2C show images representing changing aspects of a malignancy pattern of a cancer cell line by prepared si-rpS3s.

Referring to FIG. 2A, it was confirmed that, in both of the human fibrosarcoma cell line (HT1080) and the human skin melanoma cell line (WM115), the cells were changed into rounded shapes which are the shapes at a normal cell level by the si-rpS3/203, 635, 747, and 766 (SEQ ID NO. 1, 2, 3, and 4, respectively) where the expression of the rpS3 protein is regulated at the mRNA level.

Figure 2B:
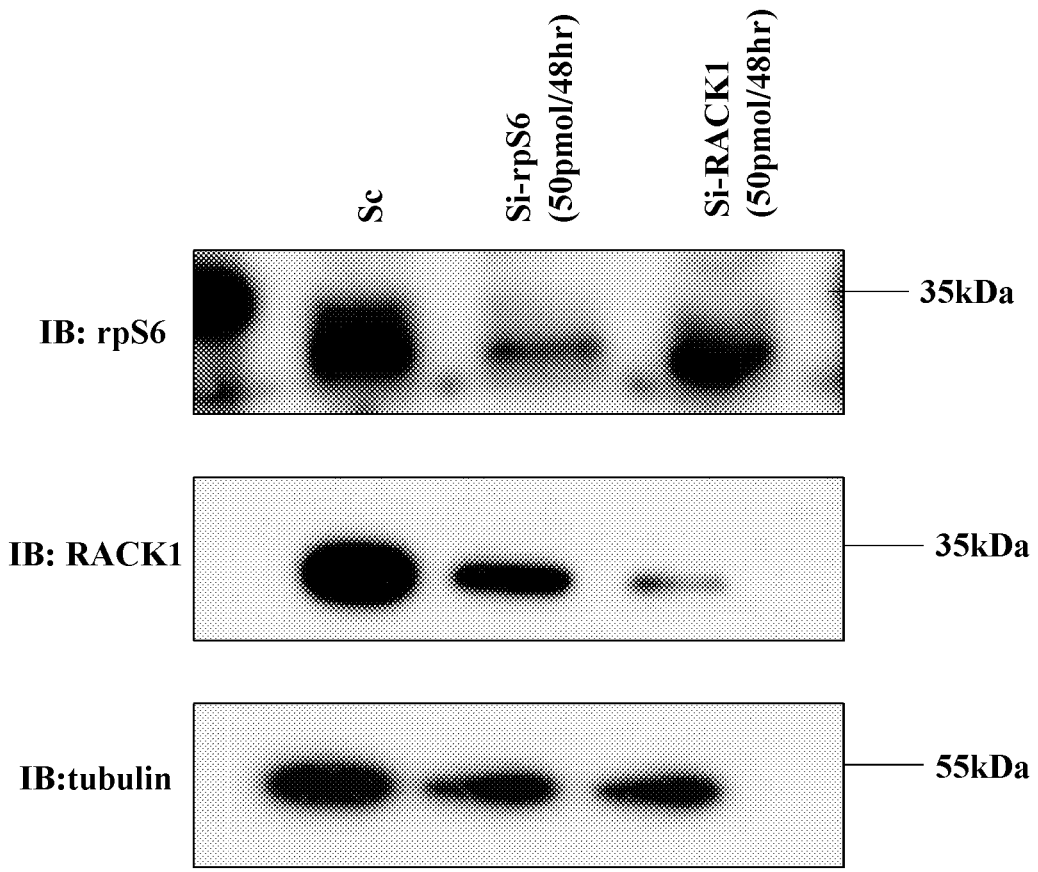
Figure 2B:
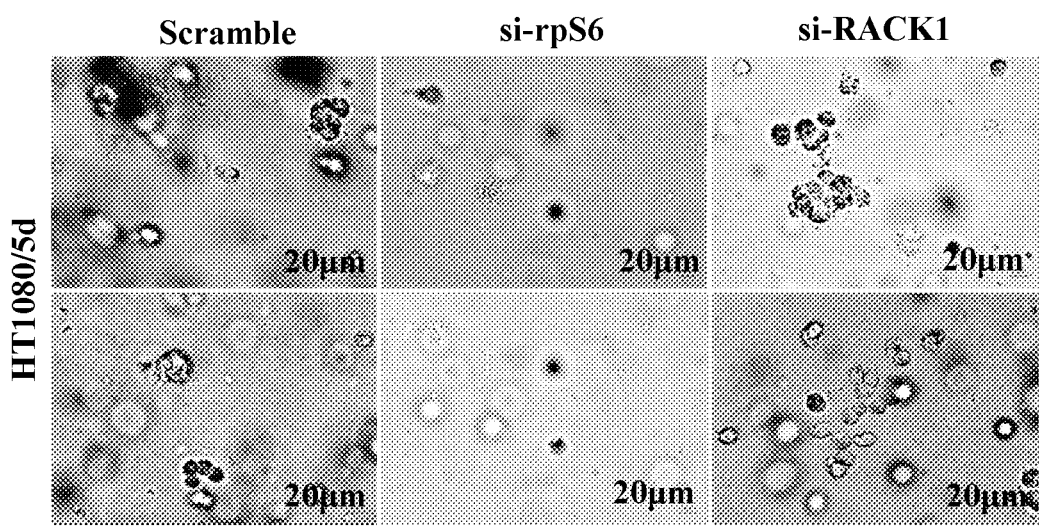

Referring to FIG. 2B, in the case of a ribosomal protein rpS6 and a RACK1 protein, any change of the cell shape the same as that of rpS3 by the si-RNA was not observed under the same experimental conditions.

Figure 2C:
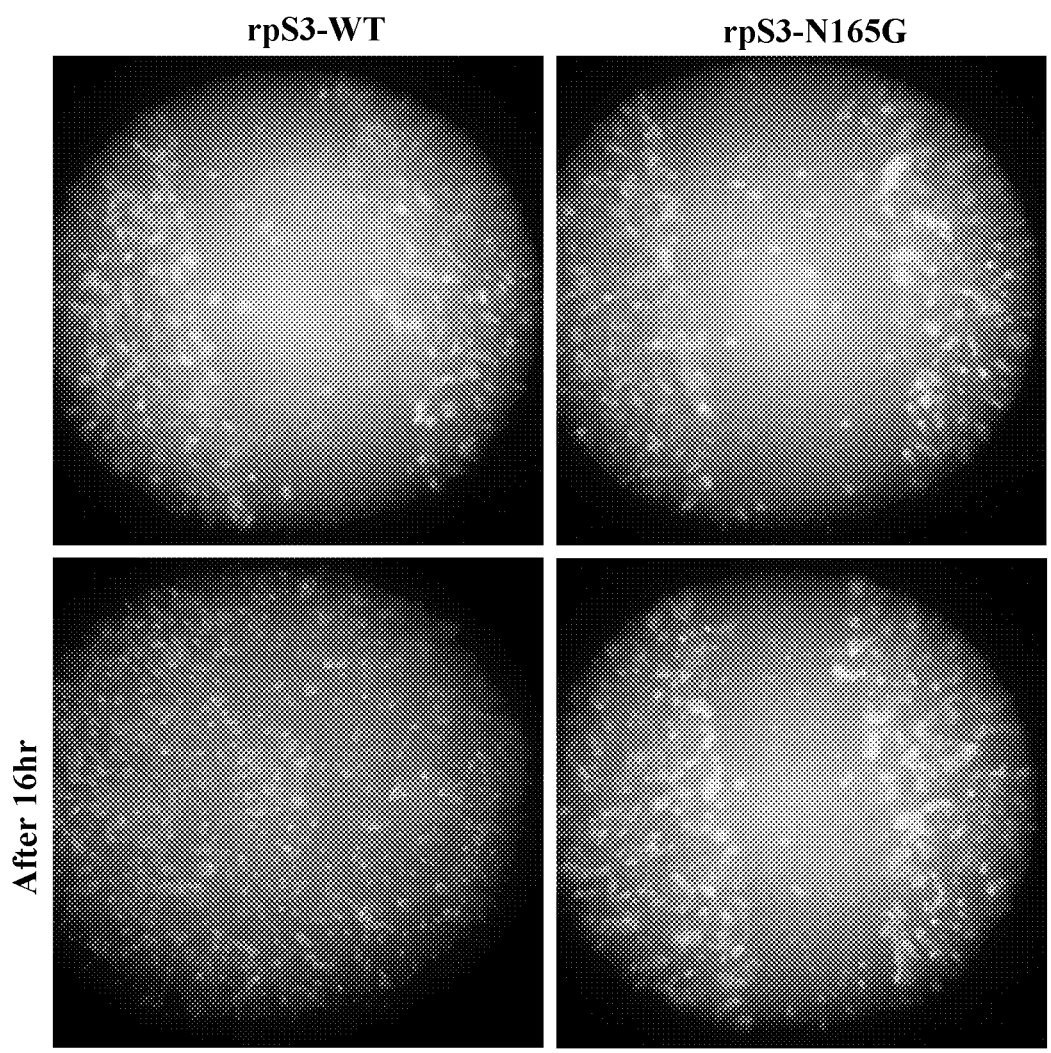

Referring to FIG. 2C, it was confirmed that the migration of the cell was remarkably lowered in an experimental group where mutant rpS3 proteins were expressed from the inspection of the migration of the cell (HT1080) in which a condition (rpS3-WT) of the expression of an original rpS3 is compared with a condition (RpS3-N165G) that a rpS3 plasmid DNA obtained by mutating the 165$^{th}$ amino acid serving as an important portion in the glycosylation process related to the secretion of the rpS3 protein is inserted and expressed.

The present invention has been described in detail according to the present invention, and it will be apparent to those skilled in the art that the specific description is only for a preferred embodiment and is not limited to the scope of the present invention. Accordingly, the actual scope of the present invention will be defined by the appended claims and their equivalents.

What is claimed is:

1. A pharmaceutical composition for inhibiting cancer cell metastasis, the pharmaceutical composition comprising at least one of:
si-rpS3/203 binding to a 203$^{rd}$ base sequence of rpS3 mRNA, wherein the si-rpS3/203 is represented by a base sequence of SEQ ID NO: 1.

2. A pharmaceutical composition for inhibiting cancer cell metastasis, the pharmaceutical composition comprising si-rpS3/635 binding to a 635$^{th}$ base sequence of rpS3 mRNA,
wherein the si-rpS3/635 is represented by a base sequence of SEQ ID NO: 2.

* * * * *